United States Patent
Walters et al.

(10) Patent No.: US 6,782,735 B2
(45) Date of Patent: Aug. 31, 2004

(54) TESTING DEVICE AND METHOD FOR VISCOSIFIED FLUID CONTAINING PARTICULATE MATERIAL

(75) Inventors: Harold G. Walters, Duncan, OK (US); Billy J. Slabaugh, Marlow, OK (US); Ronnie G. Morgan, Waurika, OK (US); Phillip C. Harris, Waurika, OK (US); Stanley J. Heath, Duncan, OK (US); Ronald J. Powell, Duncan, OK (US); David M. Barrick, Duncan, OK (US); Johnny W. Johnson, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 10/342,173

(22) Filed: Jan. 14, 2003

(65) Prior Publication Data

US 2003/0136184 A1 Jul. 24, 2003

Related U.S. Application Data (62) Division of application No. 09/499,827, filed on Feb. 8, 2000, now abandoned.

(51) Int. Cl.[7] ............................................. G01N 11/14
(52) U.S. Cl. .................................................. 73/52.28
(58) Field of Search ........................... 73/54.01, 54.23, 73/54.28, 54.33, 54.39, 152.19, 152.22, 54.32

(56) References Cited

U.S. PATENT DOCUMENTS

| | | | |
|---|---|---|---|
| 2,096,222 A | 10/1937 | Bock | 265/11 |
| 2,122,765 A | 7/1938 | Weiler | 265/11 |
| 2,237,743 A | 4/1941 | McIntyre | 265/11 |
| 2,266,733 A | 12/1941 | Bays et al. | 265/11 |
| 2,626,786 A | 1/1953 | McGlothlin | 259/8 |

(List continued on next page.)

FOREIGN PATENT DOCUMENTS

| | | |
|---|---|---|
| BE | 839479 | 9/1976 |
| CA | 672380 | 10/1963 |

(List continued on next page.)

OTHER PUBLICATIONS

K.L. Mackey, R.G. Morgan and J.F. Steffe, "Effects of Shear–Thinning Behavior on Mixer Viscometry Techniques," submitted to Journal of Texture Studies, Michigan Agricultural Experiment Station, Journal Article No. 12280, pp. 1–17 (Apr. 1, 1987).

(List continued on next page.)

*Primary Examiner*—Hezron Williams
*Assistant Examiner*—John Fitzgerald
(74) *Attorney, Agent, or Firm*—John W. Wustenberg; E. Harrison Gilbert, III (57) ABSTRACT

A device and a method for testing a viscosified fluid containing particulate indicate when the particulate is in suspension within the fluid and when it is not. The device and method stir the fluid and particulate mixture for a time during which the viscosity of the fluid changes such that during a first period of the stirring time substantially all the particulate remains suspended in the fluid and during a second period of the stirring time substantially all the particulate settles out of suspension in the fluid. A signal is generated during the first and second periods such that the signal has a characteristic that changes from the first period to the second period to indicate the change in particle carrying ability of the fluid. Other characteristics, including crosslinking time, can also be determined. A test chamber includes interacting projections extending from the inner surface of a cup receiving the fluid and from an axial support extending into the fluid in the cup.

16 Claims, 5 Drawing Sheets

U.S. PATENT DOCUMENTS

| | | | | |
|---|---|---|---|---|
| 2,953,016 A | | 9/1960 | Seitz, Jr. ............... | 73/60 |
| 3,027,756 A | | 4/1962 | Head ..................... | 73/53 |
| 3,053,079 A | | 9/1962 | Miller et al. ............ | 73/60 |
| 3,071,962 A | * | 1/1963 | Perkins, Jr. ............ | 73/54.01 |
| 3,269,171 A | | 8/1966 | Bruss et al. ............. | 73/60 |
| 3,285,057 A | | 11/1966 | De Zurik ............... | 73/59 |
| 3,292,423 A | | 12/1966 | Banks ................... | 73/60 |
| 3,347,089 A | | 10/1967 | Perry .................... | 73/59 |
| 3,402,729 A | | 9/1968 | Richmond et al. ....... | 137/92 |
| 3,435,666 A | | 4/1969 | Fann ..................... | 73/60 |
| 3,636,753 A | | 1/1972 | Thiele et al. ............ | 73/59 |
| 3,751,975 A | | 8/1973 | Katsura .................. | 73/59 |
| 3,803,903 A | | 4/1974 | Lin ...................... | 73/59 |
| 3,857,295 A | | 12/1974 | Simons .................. | 73/64.1 |
| 3,875,791 A | | 4/1975 | Fitzgerald et al. ........ | 73/59 |
| 4,044,602 A | | 8/1977 | Higgs et al. ............. | 73/59 |
| 4,065,959 A | | 1/1978 | Richardson .............. | 73/56 |
| 4,151,744 A | | 5/1979 | Hemmings ............... | 73/54 |
| 4,157,036 A | * | 6/1979 | Kivenson ................ | 73/290 R |
| 4,175,425 A | | 11/1979 | Brookfield .............. | 73/59 |
| 4,181,023 A | | 1/1980 | Clamroth et al. ......... | 73/432 R |
| 4,184,364 A | | 1/1980 | Du Bae .................. | 73/54 |
| 4,283,938 A | | 8/1981 | Epper et al. ............. | 73/59 |
| 4,299,118 A | | 11/1981 | Gau et al. ............... | 73/59 |
| 4,341,111 A | | 7/1982 | Husar .................... | 73/64.1 |
| 4,448,061 A | | 5/1984 | Brookfield .............. | 73/59 |
| 4,466,276 A | | 8/1984 | Ruyak et al. ............ | 73/59 |
| 4,468,232 A | * | 8/1984 | Funk ..................... | 44/280 |
| 4,484,468 A | | 11/1984 | Gau et al. ............... | 73/60 |
| 4,499,753 A | | 2/1985 | Carr ...................... | 73/59 |
| 4,501,143 A | | 2/1985 | Prior et al. .............. | 73/153 |
| 4,510,800 A | | 4/1985 | Prior ..................... | 73/153 |
| 4,557,142 A | | 12/1985 | Hensley et al. ........... | 73/153 |
| 4,571,988 A | | 2/1986 | Murphy, Jr. ............. | 73/60 |
| 4,592,226 A | * | 6/1986 | Weber et al. ............ | 73/54.28 |
| 4,612,800 A | | 9/1986 | Erian ..................... | 73/54 |
| 4,622,846 A | | 11/1986 | Moon, Jr. et al. ......... | 73/59 |
| 4,648,264 A | | 3/1987 | Freese et al. ............. | 73/64.1 |
| 4,653,313 A | | 3/1987 | Sabins et al. ............. | 73/61.4 |
| 4,668,911 A | | 5/1987 | Mueller et al. ........... | 324/208 |
| 4,688,588 A | * | 8/1987 | Horsley et al. ........... | 137/13 |
| 4,823,594 A | * | 4/1989 | Gray ..................... | 73/54.01 |
| 4,829,811 A | | 5/1989 | Ehlert et al. ............. | 73/59 |
| 4,879,897 A | | 11/1989 | Booth et al. ............. | 73/59 |
| 4,916,946 A | * | 4/1990 | Cameron ................ | 73/152.18 |
| 5,056,358 A | * | 10/1991 | Laskowski et al. ....... | 73/54.28 |
| 5,167,143 A | | 12/1992 | Brookfield .............. | 73/54.23 |
| 5,321,974 A | | 6/1994 | Hemmings et al. ....... | 73/54.31 |
| 5,535,619 A | | 7/1996 | Brookfield .............. | 73/54.33 |
| 5,546,791 A | | 8/1996 | Meeten .................. | 73/54.28 |
| 5,604,300 A | * | 2/1997 | Sayers et al. ............ | 73/54.31 |
| 5,684,247 A | | 11/1997 | Preikschat .............. | 73/54.32 |
| 5,799,734 A | | 9/1998 | Norman et al. .......... | 166/278 |
| 6,467,340 B1 | * | 10/2002 | Gallagher et al. ........ | 73/152.18 |

FOREIGN PATENT DOCUMENTS

| | | |
|---|---|---|
| DE | 1184119 | 12/1964 |
| RU | 415553 | 7/1974 |
| RU | 568869 | 11/1977 |
| RU | 594438 | 2/1978 |
| RU | 670855 | 6/1979 |

OTHER PUBLICATIONS

Publication entitled "TT100 In–Line Vicometer," 5 pp., Brookfield Engineering Laboratories, Inc., Stoughton, Mass. (Sep. 1988).

Publication entitled "TT200 Process Viscometer," 4 pp., Brookfield Engineering Laboratories, Inc., Stoughton, Mass. (Jun. 1990).

Document entitled "Description of Stirring Chamber," 5 pp. (believed to be published or to disclose device used or sold prior to Jan. 1999).

Schematic drawing entitled "Modified GAS–CHEK™ Slurry Cup," High Pressure Consistometer, p. 9, Halliburton Services (believed to be published or to disclose device used or sold prior to Jan. 1999).

Publication entitled "Cement Slurry Measurement Instruments For Laboratory," 1 p., Halliburton Services (believed to be published prior to Jan. 1999).

Publication entitled "Cement Measuring and Testing Instruments," 2 pp., Halliburton Services (believed to be published prior to Jan. 1999).

J.R. Cameron, D.C. Gardner and R.W. Veatch, Jr., "New Insights on the Rheological Behavior of Delayed Crosslinked Fracturing Fluids," SPE 18209, Society of Petroleum Engineers (1988).

F.L. Sabins, J.M. Tinsley, and D.L. Sutton, "Transition Time of Cement Slurries Between the Fluid and Set State," SPE 9285, Society of Petroleum Engineers (1980).

Publication entitled "Oil Well Cement Testing Equipment, Atmospheric Pressure Consistometer," 2 pp., Chandler Engineering Co., Tulsa, Okla. (1982).

Publication entitled "RheoChan Rotational Rheometer, Model 7400," 6 pp., EG&G Chandler Engineering, Tulsa, Okla. (believed to be published prior to Jan. 1999).

Publication entitled "Nowsco News, Compact Pressurized Consistometer," 2 pp., Nowscow Well Service Ltd., Calgary, Alberta, Canada (believed to be published prior to Jan. 1999).

Publication entitled "Section 8, Thickening Time Tests," pp. 22–28, American Petroleum Institute (believed to be published prior to Jan. 1999).

* cited by examiner

TESTING DEVICE AND METHOD FOR VISCOSIFIED FLUID CONTAINING PARTICULATE MATERIAL

CROSS-REFERENCE TO RELATED APPLICATION

This application is a divisional of co-pending application Ser. No. 09/499,827 filed Feb. 8, 2000, now abandoned.

BACKGROUND OF THE INVENTION

This invention relates generally to devices and methods that are used to test viscosified fluids, especially ones containing particulate material (subsequently referred to simply as "particulate"). The particular field of use is the oil and gas industry.

Various types of fluids are used in the oil and gas industry. Non-limiting examples include drilling muds, cement slurries, and stimulation treating fluids. Such fluids are typically pumped into oil or gas wells in known manners. It is desirable to know various characteristics of the fluids to determine how such fluids will act upon being pumped and placed in, or circulated through, the wells.

Viscosity, elasticity, and consistency are rheological characteristics that sometimes need to be measured for a given fluid. Known devices used to test fluids for these characteristics include viscometers, rheometers, and consistometers.

Some fluids used in oil or gas wells carry particulate, and it is typically desired that such fluids support the particulate in suspension for at least some period of time. That is, the particulate is preferably dispersed throughout the volume of a particular fluid during at least part of the time the fluid is used in a well. For example, a fracturing fluid might include a base fluid in a gel form and a quantity of particulate referred to as a propping agent or proppant. An example of a propping agent or proppant is sand. The base fluid preferably supports the proppant such that the proppant is suspended in the fluid during the time the mixture is pumped into a well. The pumping is under pressure sufficient for the fluid to hydraulically fracture a selected zone of the earth traversed by the well. After fracturing, the fluid may be flushed out with the flow of hydrocarbons from the fractured zone, but the propping agent preferably remains in place to prop the fractures open.

A typical fluid used to transport particulate has a viscosity that changes during the time the fluid is used in a well. Viscosity is defined as the ratio of shear stress to shear rate (velocity gradient). If this ratio changes with shear rate, this may be referred to as "apparent viscosity function." Viscosity is one parameter of the fluid that defines the fluid's ability to support the particulate in suspension. However, to measure a single viscosity point or the apparent viscosity function does not directly indicate the time during which the fluid will support particulate in suspension and the time during which the fluid will not. That is, a measurement that merely shows a changing viscosity does not indicate when the particulate is in suspension within the fluid and when it is not (i.e., when the particulate has settled out of the fluid). Thus, there is the need for a device and method which can test fluids to determine times during which particulate is suspended in the fluid and times during which particulate settles out of suspension. There is the more particular need for a device and method to measure the viscous and elastic properties of a fluid, both with and without particulate, under dynamic conditions at elevated temperatures and pressures at a variety of shear rates and in such a way as to directly indicate particle transport, suspension and settling. At least one embodiment of such a device and method preferably should also be suitable for use at a well site to measure crosslink time of a fluid being pumped into the well.

SUMMARY OF THE INVENTION

The present invention meets the foregoing needs by providing a novel and improved device and method for testing viscous and/or elastic fluids, including ones containing particulate. Such device and method directly indicate time periods during which a tested fluid is supporting particulate in suspension and when the tested fluid is not (i.e., when the particulate is settling out of suspension).

A particular implementation of the device of the present invention may be referred to as a high-pressure, high-temperature mixer viscometer that can measure viscous and elastic properties and crosslink and particulate transport time. This implementation includes a paddle type of mixing device which has one or more flags, paddles, or vanes which rotate in or around the fluid to be tested and two or more flags, paddles or vanes in a torque sensing structure. The device is capable of measuring varying volume average shear rates and volume average shear stresses, signifying varying viscosities, and is especially useful at low shear rates. This device can condition the fluid under test at low, ambient, and elevated temperatures and pressures. This device provides an output that can be used to measure or indicate viscous and elastic properties of the test fluid (which can be with or without particulate material), the change in fluid properties with time (e.g., crosslink time), particle transport (particle suspension and particle settling), and particle-to-particle interactions and degree of adhesive coating on particles (e.g., higher torque readings for more particle-to-particle interaction, such as from higher particle concentrations, or for increased adhesive coating).

The present invention provides a mixer viscometer which comprises: a receptacle having a cavity to receive a viscosified fluid containing particulate; means for closing the cavity after viscosified fluid containing particulate is placed therein such that the closed cavity defines a continuous test chamber which can be pressurized above atmospheric pressure; means for stirring the fluid in the test chamber such that particulate in the fluid is suspended in the fluid during one period of time of the stirring but is not suspended in the fluid during another period of time of the stirring; and means for generating a signal in response to the stirring during both periods of time. The means for stirring preferably includes at least one projection extending into the cavity from an inner surface of the receptacle defining the cavity.

Another definition of the present invention is as a particle transport capability detector apparatus which comprises: a viscometer including a viscometer cup and further including an axial shaft disposed within the cup when a fluid to be tested is in the cup; at least two projections extending laterally outward from the axial shaft of the viscometer; and at least one projection extending laterally inward from an inner surface of the viscometer cup, wherein the projections effect stirring of fluid in the cup in response to rotation of at least one of the cup or axial shaft of the viscometer.

A viscometer test chamber of the present invention comprises: a slurry cup; a pressure-sealed end closure for the slurry cup; a support hanging below the end closure into the slurry cup when the end closure is connected to the slurry cup to close the slurry cup; not more than four vertical planar projections extending laterally outward from the support; and not more than four vertical planar projections extending laterally inward from an inner surface of the slurry cup, wherein the projections effect stirring of fluid in the slurry cup in response to rotation of at least one of the slurry cup or support.

The present invention also provides a method of testing for particulate transport time of a fluid containing particulate. The method comprises stirring, for a time during which the viscosity or elasticity of the fluid changes, a fluid containing particulate such that during a first period of the stirring time substantially all the particulate remains suspended in the fluid and during a second period of the stirring time substantially all the particulate settles out of suspension in the fluid. The method further comprises generating a signal during the first and second periods such that the signal has a characteristic that changes from the first period to the second period to indicate the change in particulate carrying ability of the fluid.

The method of the present invention can also be defined as comprising: using in a high-pressure, high-temperature viscometer a container having at least one inward projection and using in the viscometer an axial support having at least two outward projections, wherein the container holds a viscous and/or elastic fluid containing particulate and the support extends into the fluid; creating relative movement between the container and the support, and the projections thereof; and generating a measurement signal in response to a characteristic of the viscometer occurring by creating the relative movement such that the measurement signal indicates an elastic particulate transport time period and a viscous settling time period. In a particular implementation, generating a measurement signal includes generating an electric signal in response to torque related to creating relative movement between the container and the support and the projections thereof. The measurement signal also may indicate, prior to the elastic particulate transport time period and the viscous settling time period, a crosslinking time during which the fluid becomes viscoelastic.

Still another definition of the method of testing a viscosified fluid containing particulate comprises: mixing sand and a basegel to form a sand-gel slurry mixture; putting at least a portion of the mixture in a slurry cup having at least two inward projections extending inward from an inside surface of the cup; connecting the slurry cup in a viscometer having an axial support from which at least two outward projections extend outward; increasing pressure in the connected slurry cup such that pressure on the mixture in the cup is greater than atmospheric pressure; creating relative movement between the slurry cup and the axial support, and the projections thereof, such that the projections impart a stirring force in the fluid under pressure; and generating a measurement signal in response to a characteristic of the viscometer occurring by creating the relative movement. The method may further comprise heating the mixture in the slurry cup to a temperature greater than ambient temperature (and preferably greater than 212° F.).

Still a further definition of the present invention is as a method of testing a fluid containing particulate, comprising: using in a viscometer a cup having at least one inward projection and using in the viscometer an axial support having at least two outward projections, wherein the cup receives fluid containing particulate and the support extends into the fluid; creating relative movement between the cup and the support, and the projections thereof; and generating a measurement signal in response to a characteristic of the viscometer occurring by creating the relative movement such that the measurement signal indicates a crosslinking time for the fluid. The method of the present invention may further comprise placing in the container at a well site a sample of the fluid taken from a stream of the fluid as the stream is flowing into the well, and performing the using, creating and generating steps at the well site as the stream is flowing into the well.

Therefore, from the foregoing, it is a general object of the present invention to provide a novel and improved device and method for testing viscous and/or elastic fluids, including ones containing particulate. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 15 is a graph showing a response to crosslinking in the test fluid and such fluid becoming viscoelastic.

DETAILED DESCRIPTION OF THE INVENTION

A type of fluid with which the present invention can be used is referred to as a viscous and/or elastic fluid whose viscosity changes over time. One such fluid is a viscoelastic fluid that may typically go through different phases over time; for example, from an initial uncrosslinked state, to a crosslinked elastic state, to a viscous settling state. The particulate to be used in the fluid can be, for example, sized sand, resin coated sand, sintered bauxite beads, metal beads or balls, ceramic particles, glass beads, polymer resin beads, ground nut shells and the like. The particulate size may be of any suitable size, with typical sizes being within the range from about 8 to about 170 on the U.S. Sieve Series scale. The foregoing are non-limiting examples. A more general statement about a mixture for which the present invention is particularly intended is that it is a mixture of a particulate and a fluid which during one period of time is able to support the quantity of particulate in suspension under a stirring action but which during another period of time is unable to support the particulate in suspension even under the stirring action. The invention also measures viscous and/or elastic properties of the fluid itself without sand. Examples include drilling muds, cement slurries, and stimulation treating fluids used in the oil and gas industry.

Figure 1:
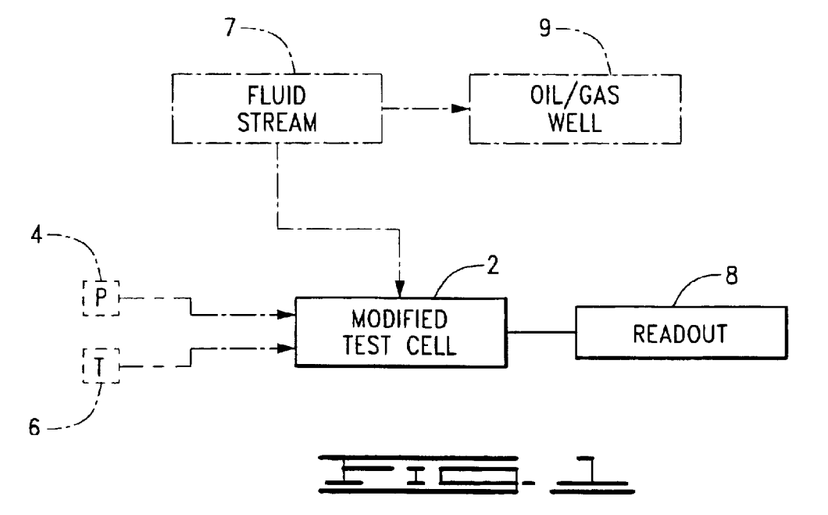
FIG. 1 is a block diagram of a viscometer having a modified test cell implementing a preferred embodiment of the present invention, which viscometer is illustrated in an environment at an oil or gas well site and which viscometer can be an open-cup type or a high-pressure and/or high-temperature type.

One preferred embodiment device of the present invention that tests a fluid such as described above is implemented with a high-pressure (above ambient), high-temperature (above 212° F.) viscometer which includes a receptacle to receive the fluid to be tested and which also includes a support that is disposed in the receptacle (and thus also in the fluid) when the fluid is in the receptacle to be tested. Such a viscometer can be a conventional one (e.g., a Fann model 50 viscometer) but adapted to the present invention by a modified test cell 2. The present invention can also be used with, or incorporate, a conventional open-cup or atmospheric viscometer (e.g., a Fann model 35 viscometer), but also adapted by a modified test cell 2. In either case, this modified test cell 2 includes at least one projection extending laterally inward from an inner surface of the receptacle mentioned above and forming part of the modified test cell 2. The modified test cell 2 also preferably includes at least two projections extending laterally outward from the support mentioned above. Such device of the present invention is depicted in FIG. 1 and can otherwise comprise conventional components of a high-pressure, high-temperature viscometer, including pressure control 4, temperature control 6, and readout 8, or of an atmospheric type viscometer that does not have at least the pressure control 4. As also shown in FIG. 1, either embodiment can be used at a well site to receive in real time a sample of the mixture from a fluid stream 7 flowing into an oil or gas well 9.

Figure 2:
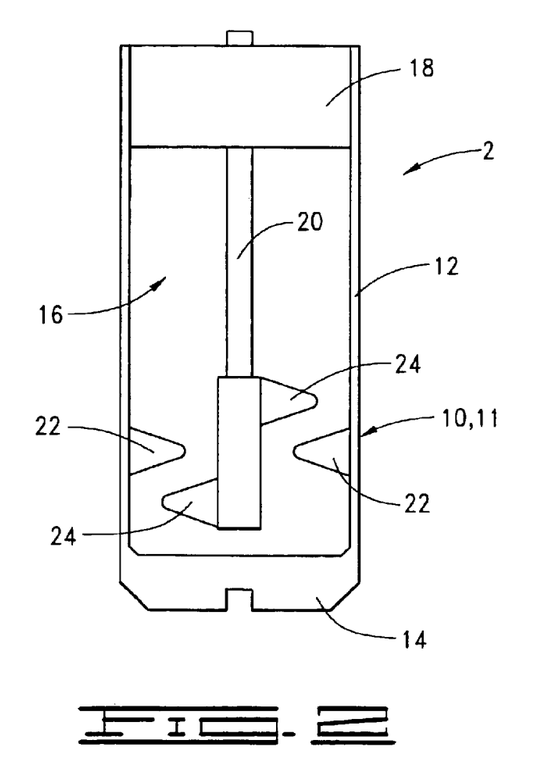
FIG. 2 is a schematic illustration of the modified test cell of a particular implementation of the preferred embodiment.

A particular implementation of the modified test cell 2 for high-pressure use is represented in FIG. 2. A receptacle 10 includes a conventional slurry cup 11 of a conventional viscometer of the high-pressure, high-temperature type referred to above. The receptacle 10 has a cylindrical side wall 12 extending from an end closed by a bottom wall 14 to an open end opposite the bottom wall 14. The side wall 12 and the bottom wall 14 have inner surfaces defining a cavity 16 in the receptacle 10. The cavity 16 receives the fluid to be tested. This cavity 16 provides a single continuous volume or cell for the fluid to be tested.

The modified test cell 2 of the FIG. 2 embodiment also includes means for closing the open end of the cavity 16 or receptacle 10 after the fluid is placed in the cavity 16. This closing means completes the definition of the outer boundaries of the continuous test chamber which can be pressurized above atmospheric pressure. In the implementation of FIG. 2, the closing means includes a conventional pressure sealed end closure 18 for the slurry cup 11 defining the receptacle 10. The closing means also includes the aforementioned support, which in the FIG. 2 implementation is an axial shaft, or axial support 20. This axial shaft hangs below the end closure 18 into the slurry cup 11 when the end closure 18 is connected to the slurry cup 11 in conventional manner to close the slurry cup 11. One example of the end closure 18 and the axial shaft 20 is found in the aforementioned Fann model 50 viscometer; however, other high-pressure, high-temperature devices can be used (and as mentioned, the present invention has application with devices that need not have high-pressure or high-temperature capability, such as an open-cup viscometer).

The modified test cell 2 shown in FIG. 2 further includes means for stirring fluid in the test chamber such that particulate in the fluid is suspended in the fluid during one period of time of the stirring but is not suspended in the fluid during another period of time of the stirring. This is implemented in FIG. 2 by at least one projection extending into the cavity 16 from the inner surface of the receptacle 10. In FIG. 2, two flat, substantially triangular metallic projections 22 are connected to the inner surface of the receptacle 10 diametrically opposite each other. Connection can be by any suitable means, including but not limited to welding to or integrally machining with the side wall 12. In other embodiments, a single projection 22 can be used or more than two projections 22 can be used.

The FIG. 2 implementation also includes at least two projections extending laterally outward from the axial support 20, preferably in a rotationally balanced configuration and positioned to have desired sensitivity to settling particulate. Two diametrically opposed, axially spaced projections 24 of the same type as projections 22 are connected to the axial shaft 20 in the FIG. 2 embodiment. While there may be two or more projections 24, preferably there is an even number of these projections. Connection can be by any suitable means, including but not limited to welding to or integrally machining with the axial support 20 or a mandrel that connects to the axial support 20.

The projections 22, 24 are large enough to generate a torque during stirring, but small enough to produce a torque reading within a desired range (the larger the projections, the larger the torque reading) and to leave a gap between the set of projections 22 and the set of projections 24 sufficient for the particulate material to pass through without bridging (e.g., three to four particle diameters).

The projections 24 operatively cooperate with the projections 22 to effect stirring of fluid in the slurry cup 11 in response to rotation of at least one of the slurry cup 11 or axial support 20. Typically the slurry cup 11 is rotated so that the projections 22 principally effect the stirring, and the projections 24 are deflected in response to thereby sense torque. This rotation is achieved in conventional manner within the remainder of the viscometer used to implement the described embodiment of the present invention. The rotation to be imparted is such that mixing of the particulate in suspension within the fluid occurs during a period of the stirring time in which the fluid is still able to support the particulate, but the rotation is not such that mixing occurs when the fluid is no longer able to support the particulate in suspension, whereby the particulate settles out of suspension. The rotation is also obtained in a manner that permits an appropriate readout signal to be generated. Such rotation is typically within the range between one revolution per minute and one thousand revolutions per minute.

As mentioned above, the embodiment of the present invention shown in FIGS. 1 and 2 includes a readout 8. This is part of a means for generating a signal in response to the stirring of the fluid during both the period during which particulate suspension occurs and the period during which particulate settling occurs. This is implemented in FIG. 2 by using the two or more projections 24 on the axial shaft 20. For example, when the slurry cup 11 is rotated, torque is sensed through the axial shaft 20 in known manner. In an embodiment in which the axial shaft 20 is rotated to effect mixing by the projections 24, torque is sensed through the slurry cup 11 or the axial shaft 20 in known manner. For the modified test cell 2 of the illustrated embodiment, the sensitivity of the readout 8 to such torque can be adjusted by using different strengths of springs or different sizes of flags (projections) or different transducers. For example, for a Fann Model 50 viscometer, a lighter weight spring is used in the present invention as compared to the spring used in the conventional viscometer construction and operation. An electric signal is generated in known manner in response to the deflection of the axial shaft 20; and the electric signal is used in known manner to create a display, such as an electronic display or a printed graph. As explained further hereinbelow, the display is maintained so that a graph of the response over time is obtained in accordance with the present invention.

Figures 3, 4, 5, 6, 7, 8:
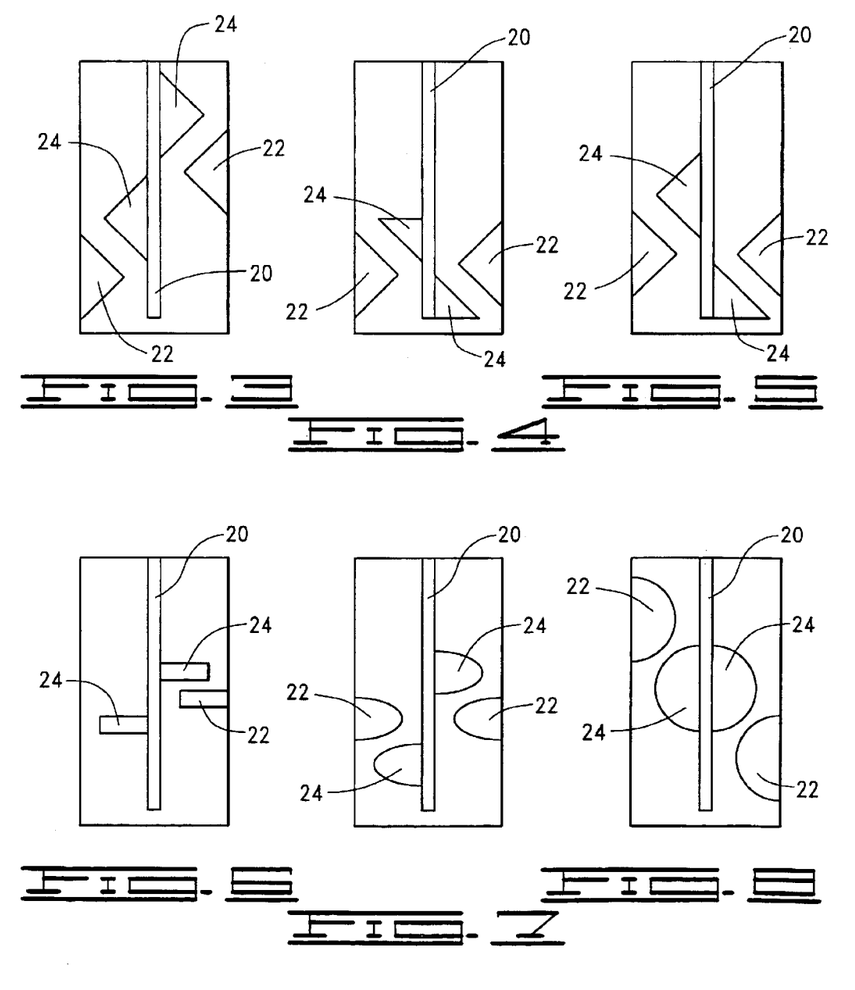
FIG. 3 is a representation of another configuration of projections in the present invention.
FIG. 4 is a representation of a further configuration of projections in the present invention.
FIG. 5 is a representation of still another configuration of projections in the present invention.
FIG. 6 is a representation of a still further configuration of projections in the present invention.
FIG. 7 is a representation of yet another configuration of projections in the present invention.
FIG. 8 is a representation of a further configuration of projections in the present invention.
Figure 9:
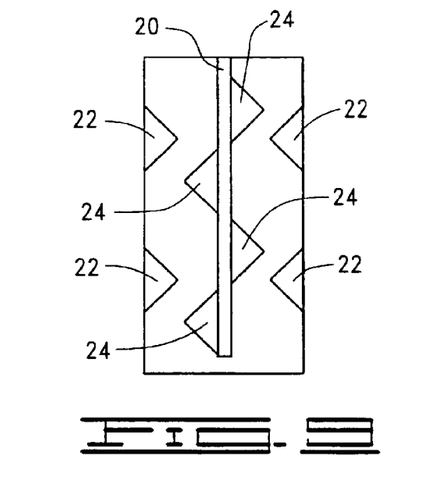
FIG. 9 is a representation of another configuration of projections in the present invention.
Figure 10:
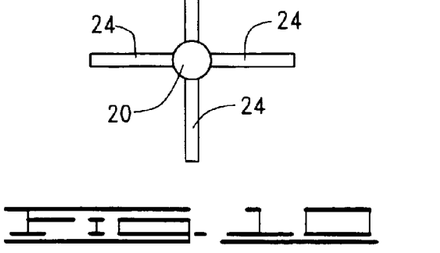
FIG. 10 is a plan view representation of four projections spaced around an axial support.
Figure 11:
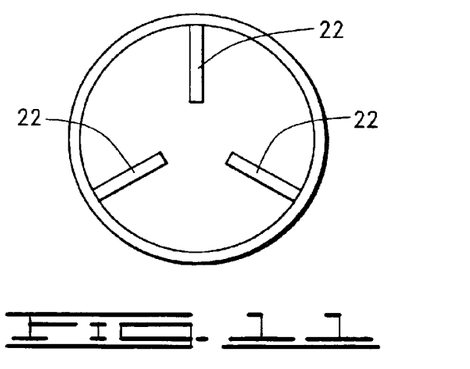
FIG. 11 is a plan view representation of three projections spaced around an inner surface of a cup for holding a fluid to be tested.
Figure 12:
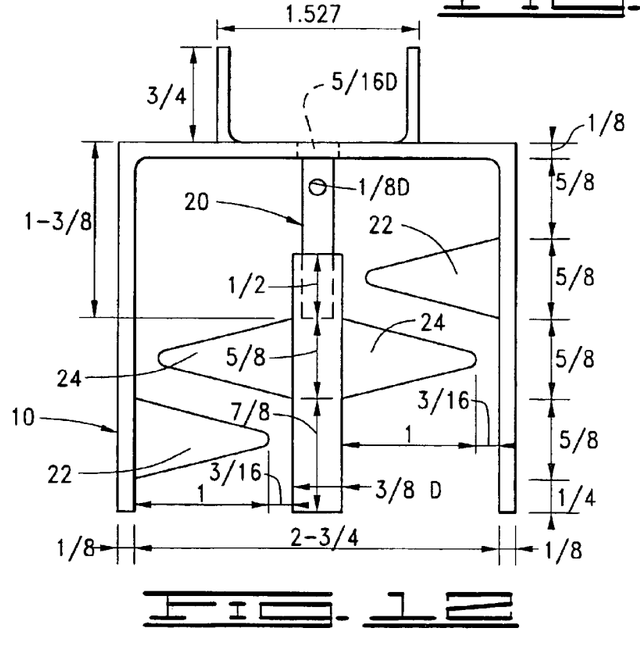
FIG. 12 represents yet another configuration of projections in the present invention, with dimensions for a particular implementation.

The projections 22, 24 and their inter-relationships with each other and the overall viscometer and method of the present invention can take different configurations. Some examples are represented in FIGS. 3–12. FIGS. 4, 5 and 7 show respective projections 24 extending from the respective axial support 20 which are axially spaced along the axial support 20, and respective projections 22 extending from the slurry cup 11 which are axially aligned (i.e., on the same circumference of the inner surface of the side wall 12). FIG. 3 shows respective projections 24 extending from the respective axial support 20 which are axially spaced along the axial support 20, and respective projections 22 extending from the slurry cup 11 which are axially spaced. FIG. 8 shows projections 24 extending from the axial support 20 which are axially aligned along the axial support 20, and projections 22 extending from the slurry cup 11 which are axially spaced. FIG. 9 shows axially spaced projections 24 with projections 22 in axially spaced groups, in which groups the projections 22 are axially aligned. FIG. 6 shows two axially spaced projections 24 from the axial shaft 20 and a single projection 22 from the side wall 12. FIG. 10 illustrates four projections 24 equally spaced around the axial shaft 20, and FIG. 11 illustrates three equally spaced projections 22 from the slurry cup 11. The projections of FIGS. 3, 4, 5 and 9 are triangular, those in FIG. 6 are rectangular, the ones in FIG. 7 are elliptical, and the projections in FIG. 8 are semicircular. FIG. 12 illustrates a specific implementation of triangular projections 22, 24 on the receptacle 10 and the axial shaft 20, respectively (the receptacle 10 is the rotated member in this embodiment, such as in a Fann model 35 viscometer modified with the projections 22, 24 of the present invention, and in use is immersed in the fluid held by an outer container of a type used in the art).

The projections 22, 24 of the preferred embodiments are flat, planar members that are disposed vertically (i.e., the major planar surfaces of such member are vertical) as depicted in the drawings. The projections 22, 24 also are sized such that not more than four would typically be used along the vertical or axial direction on either the axial shaft 20 or the receptacle 10. Indeed, in the particular embodiment of FIG. 12, there is only a single vertical group on the axial shaft 20 and two vertically spaced projections or groups on the receptacle 10 (in FIG. 12, the dimensions shown are in inches and each projection 22, 24 has a base $\frac{5}{8}$-inch wide, a length of 1 inch and a width or thickness of $\frac{1}{8}$ inch; the projections 22, 24 are disposed within a space of $1\frac{7}{8}$ inches of the overall receptacle 10 body height of $2\frac{7}{8}$ inches). See also FIGS. 2–11. The projections 22, 24 are made of any material suitable for the substances, pressures, temperatures, and rotational characteristics to be encountered in using the present invention, as known in the art.

Next, the method of the present invention will be described. The preferred embodiment device described above with reference to FIGS. 1 and 2, or any suitable configuration of projections (e.g., those in FIGS. 3–12), is one device that can be used to perform the high-pressure, high-temperature embodiment of the present method; however, it is not contemplated to be the exclusive way of performing it (e.g., an open-cup configuration as shown in FIG. 12 can be used if high-pressure, high-temperature testing is not required). Likewise, the device of the present invention is not limited to the preferred embodiments described above.

With regard to using the high-pressure, high-temperature embodiment device described above, the present invention provides a method of testing a viscosified fluid containing particulate, which method comprises using in a high-pressure, high-temperature viscometer a container having at least one inward projection. It also preferably includes using in the viscometer an axial support or axial shaft having at least two outward projections. The container, also called a slurry cup, holds the fluid, and the axial support extends into the fluid. The method further comprises creating relative movement between the container and the axial support, and the projections thereof. At least one set of these projections imparts a stirring force in the fluid. Relative movement is preferably created by rotating in known manner either the slurry cup of the viscometer or the axial support of the viscometer. The method still further includes generating a measurement signal in response to a characteristic of the viscometer occurring by creating the relative movement. In the preferred embodiment, the measurement signal is an electric signal generated in response to torque related to creating relative movement between the container and the axial support and the projections thereof. Such electric signal can be generated with conventional torque sensing components of the viscometer which respond to deflection of the axial shaft by the force of the fluid against the projections on the axial shaft. Alternatively, the axial deflection may be read directly on a dial without the use of an electrical signal or signal generating means. Another preferred aspect of the foregoing is that the relative movement is created for a time during which the viscosity and/or elasticity of the fluid changes, which time includes a first period during which substantially all the particulate remains suspended in the fluid and which time includes a second period during which substantially all the particulate settles out of suspension in the fluid (such as due to the viscosity and/or elasticity of the fluid decreasing to a level which does not support the particulate). That is, rotation (e.g., by a motor connected and operated in known manner) continues throughout the range of viscosity change from the aforementioned first period through the aforementioned second period. Thus, the measurement signal taken over time has a characteristic which indicates the first period (an elastic particulate transport time period) and the second time period (a viscous settling time period). The measurement signal can also indicate, prior to the aforementioned first period, crosslinking that occurs in the fluid; in particular, it indicates a crosslinking time during which the fluid becomes viscoelastic.

As apparent from the description of the invention above, stirring preferably includes either (1) rotating the slurry cup relative to a support disposed in the fluid, wherein the slurry cup has at least one projection extending inward into the fluid from the slurry cup and the support has at least two projections extending outward into the fluid from the support, or (2) rotating the support disposed in the fluid relative to the slurry cup. The former is typically preferred because of the lighter mass of the axial shaft structure relative to the slurry cup structure.

A more specific definition of the present invention includes: mixing sand and a basegel (i.e., a liquid viscosified with a non-crosslinked polymer in solution) to form a sand-gel slurry mixture; putting at least a portion of the mixture in a slurry cup having at least two inward projections extending inward from an inside surface of the slurry cup; connecting the slurry cup in a viscometer having an axial support from which at least two outward projections extend outward; increasing pressure in the connected slurry cup such that pressure on the mixture in the slurry cup is greater than atmospheric pressure; creating relative movement between the slurry cup and the axial support, and the projections thereof, such that the projections impart a stirring force on the fluid under pressure; and generating a measurement signal in response to a characteristic of the viscometer occurring by creating the relative movement. This definition of the method, as well as any of the other definitions thereof, can also comprise heating the mixture in the slurry cup to a temperature greater than ambient temperature. This heating is applied in the preferred embodiment in a conventional manner for high-pressure, high-temperature viscometers. The following example exemplifies this more specific definition of the method of the present invention, but it is also encompassed by the other definitions described above.

EXAMPLE

Figure 13:
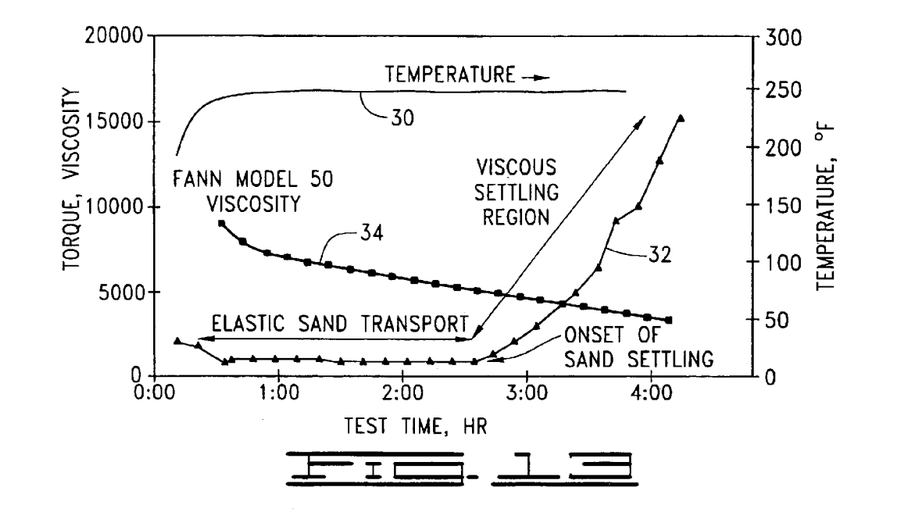
FIG. 13 is a graphical representation of a traditional viscosity measurement and temperature measurement, as well as of a particle transport capability measurement in accordance with the method of the present invention, for a particular example of a viscosified fluid.

Weigh out 20/40 mesh sand (145 grams (g) per 100 milliliters (mL) of basegel) and place in an oven preheated to 180° F., heating until the sand is at 180° F. Preheat Fann model 50 viscometer oil-bath to test temperature of 250° F. Mix one liter (L) of basegel fluid in a Waring blender using 0.30 g/L of guar polymer, 0.03 g/L of sodium bicarbonate and 0.12 g/L of sodium thiosulfate in water. Place 500 mL of the mixed basegel in a beaker and the empty viscometer test chamber cup with inward projections in 140° F. water bath and allow temperature to equilibrate. Put 100 mL of 140° F. basegel and 145 g of 180° F. sand in a mixing beaker and stir with an electric stirrer at moderately high speed. Add additives (e.g., surfactants), breakers (e.g., enzymes or oxidizers) and crosslinker (e.g., titanate, zirconate, or borate complexes) in desired test amounts. Start stopwatch. Mix until a mushroom dome appears and the gel supports sand (usually around 20 seconds). Transfer the sand-gel slurry mixture to the heated cup. Quickly place the cup on a Fann model 50 viscometer modified with the axial support having the outward projections, and pressurize the test chamber defined in the cup (target time 1:00 minute). Start the cup rotation at 25 revolutions per minute, initiate heating, and record torque data. Plot the torque and temperature data versus time. Referring to FIG. 13, the temperature graph is marked with the reference number 30 and the torque measurement obtained in accordance with the present invention is marked with the reference number 32. A corresponding cross-linked gel test fluid without sand was tested at 250° F. in a standard Fann Model 50 viscometer; the corresponding torque graph is marked with the reference number 34 in FIG. 13.

From the data plots in FIG. 13, the temperature increases up to the test temperature in about 30 minutes. The line 34 shows a decrease with time in the viscosity of the cross-linked gel fluid with breaker. This curve is typical for viscosity decline and it shows no indication of whether or not the gel will support sand. The curve 32 shows the torque reading versus time from the present invention. The cross-linked gel slurry supports sand and has minimal resistance to flow for a period of time (about 2.5 hours). This is the period of elastic transport, or perfect particulate transport, where any settling is offset by the motion of the rotating slurry cup 11 and the interacting projections 22, 24. There is a slight decrease in resistance due to the decrease in viscosity of the supporting gel. At the end of the elastic transport region, an upward inflection indicates the onset of particulate settling. Beyond this point, the gel fluid loses its elasticity, and particulate settling behavior is like that in non-crosslinked fluids and is controlled by viscous effects rather than elasticity.

Figure 14:
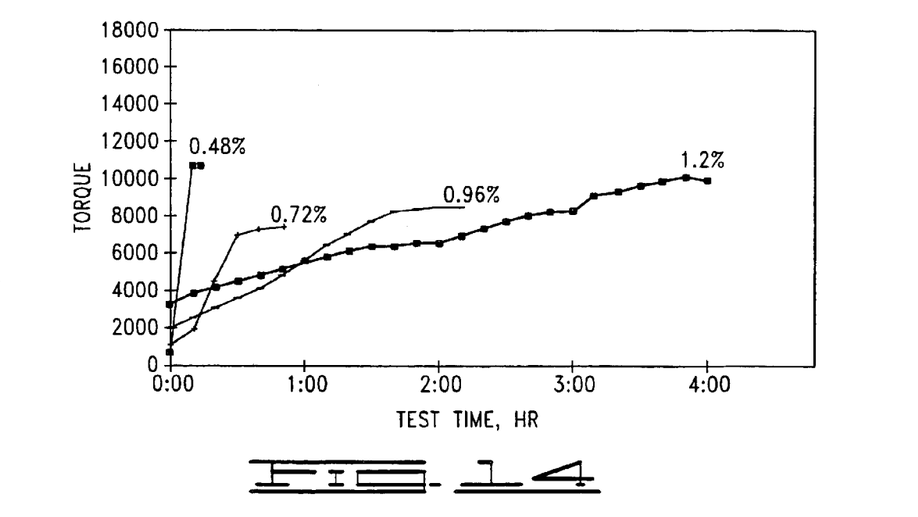
FIG. 14 is a graphical representation of measurements for modified fluids to illustrate a type of comparative analysis that can be made with the particle transport capability measurement depicted in FIG. 13.

The viscous settling region described above and illustrated in FIG. 13 can be calibrated or compared by measuring the slopes of non-crosslinked linear gel fluids containing a similar concentration of the sand or other particulate. In FIG. 14, guar polymers at concentrations of 0.48 to 1.2% were hydrated in water, sand was added to the fluid, and the slurries were measured using the present invention. All of the curves have a positive slope, indicating that sand settling occurs from the beginning of the test. There is no time where perfect proppant transport occurs. These curves may be compared to the slopes of the crosslinked gel fluids as an indication of the type of transport and effective gel concentration in the viscous settling region.

The present invention also may be used to determine crosslink time for the fluid. This occurs prior to the two time periods referred to above and typically occurs within a matter of minutes rather than several minutes or hours as in the time periods illustrated in FIG. 13. A graph showing a measurement by the mixer viscometer of the present invention responding to the fluid crosslinking and becoming viscoelastic is shown in FIG. 15. Accordingly, another definition of the method of the present invention is as a method of testing a fluid containing particulate, comprising: using in a viscometer a container having at least one inward projection and using in the viscometer an axial support having at least two outward projections, wherein the container holds the fluid which contains particulate and the axial support extends into the fluid; creating relative movement between the container and the axial support, and the projections thereof; and generating a measurement signal in response to a characteristic of the viscometer occurring by creating the relative movement such that the measurement signal indicates a crosslinking time for the fluid. The method also may include that the measurement signal be taken over time subsequent to the crosslinking time to indicate a particulate transport time period and a particulate settling time period as described above. In the preferred embodiments described herein, generating a measurement signal includes generating an electric signal in response to torque related to creating relative movement between the container and the axial support and the projections thereof.

The method may further comprise placing in the container at a well site a sample of the fluid taken from a stream of the fluid as the stream is flowing into the well, and performing the using, creating and generating steps at the well site as the stream is flowing into the well. Although any suitable embodiment described above may be used in accomplishing this, the open slurry cup embodiment (such as partially illustrated in FIG. 12) is particularly suitable because a sample of fluid can be readily extracted from the stream in known manner, poured into a beaker or other suitable container known in the art, and the beaker or container operatively placed in known manner relative to the open receptacle 10 of the FIG. 12 embodiment. This method enables real-time crosslink time testing at the well site, the results of which can then be used to modify the fluid pumped into the well.

Although the present invention is directed to the interoperative projections on the test chamber cup and axial shaft and the aforementioned method by which particle transport capability is determined, and by which crosslink time can be monitored (such as for real time use at an oil or gas well), other information can be obtained. For example, viscous and elastic properties can be determined by using the torque signal with known mathematical concepts (see, for example, U.S. Pat. No. 5,799,734; J. F. Steffe, *Rheological Methods in Food Process Engineering* (second edition), Freeman Press, East Lansing, Mich.; and K. L.

Mackey, R. G. Morgan and J. F. Steffe, "Effects of Shear-Thinning Behavior on Mixer Viscometry Techniques," Michigan Agricultural Experiment Station Journal Article No. 12280, Apr. 1, 1987; the foregoing incorporated herein by reference).

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A method of testing a fluid containing particulate, wherein the fluid has a viscosity that decreases while being stirred at a constant rotational speed, comprising the steps of:
   placing a sample of the fluid containing the particulate in a slurry cup having at least two inward projections extending inward from an inside surface of the slurry cup;
   connecting the slurry cup in a viscometer having an axial support from which at least two outward projections extend outward;
   creating continuous relative movement between the slurry cup and the axial support such that the inward and outward projections impart a stirring force in the fluid containing the particulate;
   generating a measurement signal in response to torque related to creating the relative movement between the slurry cup and the axial support; and
   analyzing the measurement signal to determine an onset of particulate settling by detecting an increase in the torque, whereby elastic particulate transport occurs during a period of time before the onset of particulate settling, and viscous settling occurs during a period of time after the onset of particulate settling.

2. The method of claim 1 wherein the measurement signal comprises an electrical signal.

3. The method of claim 1 wherein the increase in the torque is characterized by an upward inflection in a graph of the torque versus time.

4. The method of claim 1 wherein the period of elastic particulate transport occurring near the onset of particulate settling is characterized by a substantially constant torque.

5. The method of claim 1 wherein the continuous relative movement between the slurry cup and the axial support is substantially constant for a period of time before the onset of particulate settling.

6. The method of claim 1 wherein the fluid is basegel and the particulate is sand.

7. The method of claim 6 wherein substantially all the sand remains suspended in the basegel during the period of elastic particulate transport, and substantially all the sand settles out of the basegel during the period of viscous settling.

8. The method of claim 6 further comprising the step of analyzing the measurement signal to determine a crosslinking time for the basegel.

9. The method of claim 6 further comprising the steps of:
   increasing pressure in the connected slurry cup such that pressure on the basegel and the sand in the slurry cup is greater than atmospheric pressure; and
   heating the basegel and the sand in the slurry cup to a temperature greater than ambient temperature.

10. A method of testing a fluid containing particulate, wherein the fluid has a viscosity that decreases while being stirred at a constant rotational speed, comprising the steps of:
    placing a sample of the fluid containing the particulate in a slurry cup having at least two inward projections extending inward from an inside surface of the slurry cup;
    connecting the slurry cup in a viscometer having an axial support from which at least two outward projections extend outward;
    increasing pressure in the connected slurry cup such that pressure on the fluid containing the particulate in the slurry cup is greater than atmospheric pressure;
    heating the fluid containing the particulate in the slurry cup to a temperature greater than ambient temperature;
    creating continuous relative movement between the slurry cup and the axial support such that the inward and outward projections impart a stirring force in the fluid containing the particulate;
    measuring torque related to creating the relative movement between the slurry cup and the axial support; and
    analyzing the measured torque to detect an increase in the torque indicative of the onset of particulate settling;
    whereby elastic particulate transport occurs during a period of time before the onset of particulate settling, substantially all the particulate remains suspended in the fluid during the period of elastic particulate transport, viscous settling occurs during a period of time after the onset of particulate settling, and substantially all the particulate settles out of the fluid during the period of viscous settling.

11. The method of claim 10 wherein the increase in the torque is characterized by an upward inflection in a graph of the torque versus time.

12. The method of claim 10 wherein the period of elastic particulate transport occurring near the onset of particulate settling is characterized by a substantially constant torque.

13. The method of claim 10 wherein the continuous relative movement between the slurry cup and the axial support is substantially constant for a period of time before the onset of particulate settling.

14. The method of claim 10 wherein the fluid is basegel and the particulate is sand.

15. The method of claim 14 wherein substantially all the sand remains suspended in the basegel during the period of elastic particulate transport, and substantially all the sand settles out of the basegel during the period of viscous settling.

16. The method of claim 14 further comprising the step of analyzing the measurement signal to determine a crosslinking time for the basegel.

* * * * *